Figure 1:
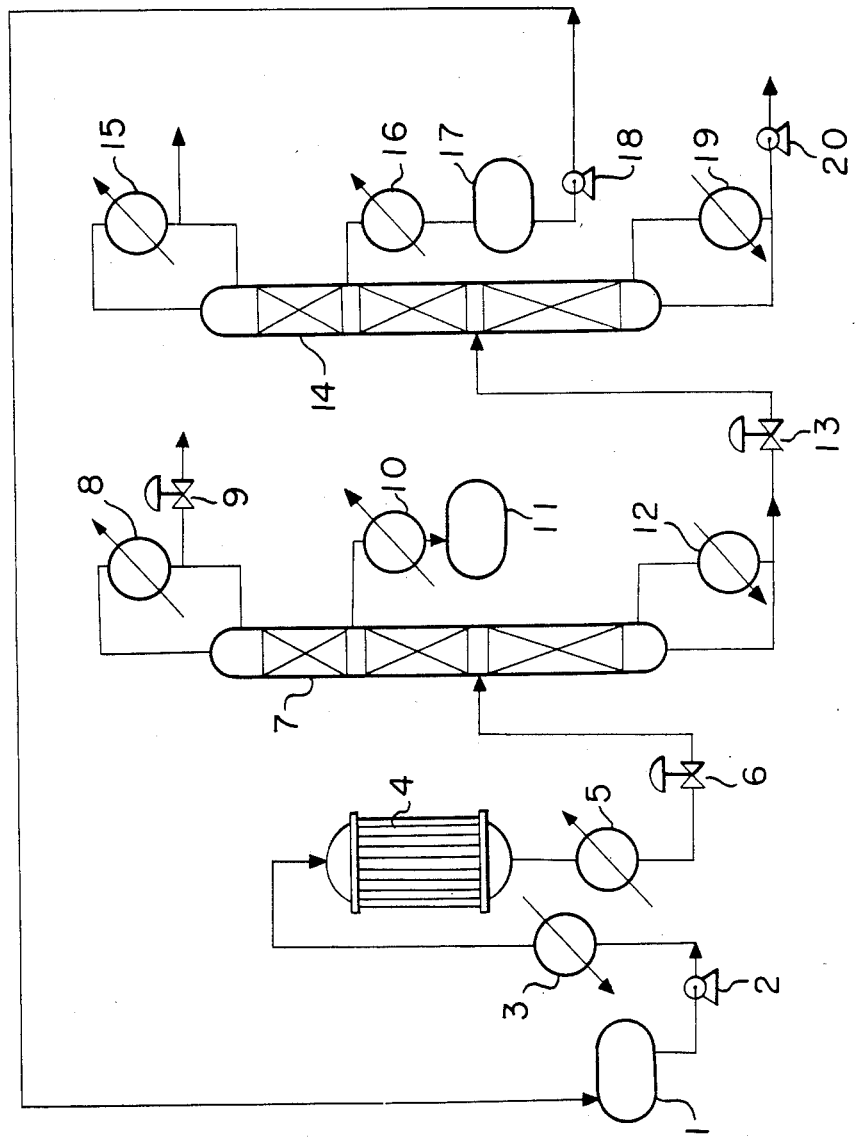

United States Patent [19]

Murai et al.

[11] Patent Number: 4,560,807

[45] Date of Patent: Dec. 24, 1985

[54] PROCESS FOR THE PRODUCTION OF DIMETHYL ETHER USEFUL AS A PROPELLANT

[75] Inventors: Nobuyuki Murai, Yokkaichi; Kazuya Nakamichi, Matsuzaka; Masayuki Otake, Yokohama; Takashi Ushikubo, Sagamihara, all of Japan

[73] Assignee: Mitsubishi Chemical Industries, Ltd., Tokyo, Japan

[21] Appl. No.: 604,943

[22] Filed: Apr. 27, 1984

[30] Foreign Application Priority Data

Apr. 27, 1983 [JP] Japan .................................. 58-74710

[51] Int. Cl.$^4$ ............................................. C07C 41/09
[52] U.S. Cl. ........................... 568/698; 203/DIG. 19; 203/DIG. 73
[58] Field of Search ............... 568/698; 203/DIG. 19, 203/DIG. 73

[56] References Cited

U.S. PATENT DOCUMENTS 2,014,408 9/1935 Woodhouse .
3,847,756 11/1974 Statman et al. .

OTHER PUBLICATIONS

Patents Abstracts of Japan, vol. 5, No. 98 (C-60) [770], Jun. 25, 1981.

*Primary Examiner*—Howard T. Mars
*Attorney, Agent, or Firm*—Oblon, Fisher, Spivak, McClelland & Maier

[57] ABSTRACT

A process for producing dimethyl ether useful as a propellant by dehydrating methanol and recovering dimethyl ether from the dehydrated product by distillation, which comprises (A) a reaction step wherein the dehydration reaction of methanol is conducted in a vapour phase under pressure of from 2 to 50 kg/cm$^2$G in the presence of a solid acid catalyst, (B) a first distillation step wherein the reaction mixture formed by the above reaction step is cooled and introduced into a pressurized distillation column under pressure of at least 5 kg/cm$^2$G; refined dimethyl ether is obtained as a side stream; substance having a boiling point lower than that of dimethyl ether is distilled from the top; and the bottom is withdrawn, and (C) a second distillation step wherein said bottom is introduced into a second distillation column under pressure lower than the pressure of the pressurized distillation column; unreacted methanol is recovered as a side stream from the second distillation column; substance having a boiling point lower than that of methanol is distilled from the top; and the bottom is withdrawn, whereby (D) the unreacted methanol recovered from the second distillation step is recycled to the reaction step.

9 Claims, 1 Drawing Figure

PROCESS FOR THE PRODUCTION OF DIMETHYL ETHER USEFUL AS A PROPELLANT

The present invention relates to a process for producing dimethyl ether from methanol. More particularly, it relates to a process for producing dimethyl ether in high purity which is extremely useful as a propellant, by efficiently separating the reaction mixture from the vapour phase dehydration reaction of methanol and recycling unreacted methanol to use it as the starting material.

As a spray propellant, Freon has been used for many years. In recent years, however, the adverse effects of Freon to the environment have been taken up as a social problem. Among various substitutes for Freon, dimethyl ether has been regarded as prospective substitute.

As a process for the production of dimethyl ether, a liquid phase dehydration has been most common wherein methanol is dehydrated by means of concentrated sulfuric acid as a catalyst. However, this process requires a substantial cost for the recovery of sulfuric acid, and it is required to have the apparatus made of a special material which is durable against the strong corrosive nature of sulfuric acid.

As a method for overcoming these difficulties, there has been proposed a vapour phase reaction wherein a solid acid catalyst is used. The most common type of the vapour phase reaction is a reaction under atmospheric pressure. However, in view of the costs involved for the separation of the dimethyl ether product, the reaction under atmospheric pressure is not economically practical.

On the other hand, it is also known to conduct the vapour phase reaction under a pressurized condition (Japanese Unexamined Patent Publication No. 40630/1981, U.S. Pat. No. 2,014,408). In particular, U.S. Pat. No 2,014,408 proposes to utilize the pressurized state of the reaction also for the subsequent separation of dimethyl ether. As far as the present inventors are aware, this process is most advantageous from the industrial point of view. However, this process has been found to be still inadequate for a new application of dimethyl ether by the present inventors. Namely, this U.S. Patent discloses a process for separating dimethyl ether, wherein at the first distillation column, a dimethyl ether fraction is obtained from the top and an unreacted methanol fraction is obtained from the bottom; at a second distillation column, said dimethyl ether fraction is separated into low boiling point components obtainable from the top and dimethyl ether obtainable from the bottom; and at a third distillation column, said unreacted methanol fraction is separated into unreacted methanol obtainable from the top and high boiling point components obtainable from the bottom. This process can be regarded as the one which most of engineers in the art are likely to adopt without any hesitation or anxiety. However, it has now been found by the present inventors that from a new viewpoint of producing dimethyl ether useful as a propellant, this process has a fatal defect concerning impurities. Since, in the vapour phase reaction under pressure, the production of impurities per one reaction is relatively small, no one in the prior art could be aware of, nor recognized the defect. However, it has been found that as the recovered unreacted methanol is recycled and reused, impurities having boiling points inbetween dimethyl ether and methanol, for instance, ethyl methyl ether, methyl formate and formal, gradually accumulate, and it has been found also that the accumulation of the impurities can reach a level as high as 20% or higher, as represented by ethyl methyl ether in the reaction product. This phenomenon appears even when high purity methanol is used as the starting material. This tendency is accelerated when by-product methanol is used as the starting material. Thus, inclusion of impurities in the dimethyl ether product is unavoidable. When this dimethyl ether product is to be used as a propellant, it has a fatal defect as an aerosol product in that it gives rise to an odor or a "wet" feeling. It is of course conceivable to sacrifice the yield of dimethyl ether in order to avoid the accumulation of the impurities. However, such is not advantageous from the industrial point of view.

The present inventors have conducted extensive researches to discover this new technical problem i.e. the accumulation of impurities, which is fatal for the production of dimethyl ether intended specifically for use as a propellant, and, overcoming the problem, to develop an industrially advantageous process for the production of dimethyl ether useful as a propellant. As a result, it has been concluded that by combining a pressurized reaction method with a specific two step distillation process, it is possible to realize superior reaction performance and highly efficient separation and purification, whereby highly pure dimethyl ether can be produced in an industrially extremely advantageous manner, and at the same time, it is possible to recover unreacted methanol in a pure state and recycle it to use it again as the starting material. The present invention is based on these discoveries and development.

It is an object of the present invention to provide a process for producing dimethyl ether in high purity and in good yield.

Another object of the present invention is to provide an industrially advantageous process for the production of dimethyl ether suitable for use as a propellant for aerosol products.

A further object of the present invention is to provide a process for the production of dimethyl ether useful as a propellant, whereby methanol starting material may not necessarily be highly pure and may be selected from a wide range of material sources.

Such objects of the present invention can readily be attained by a process for producing dimethyl ether useful as a propellant by dehydrating methanol and recovering dimethyl ether from the dehydrated product by distillation, which comprises (A) a reaction step wherein the dehydration reaction of methanol is conducted in a vapour phase under pressure of from 2 to 50 kg/cm$^2$G in the presence of a solid acid catalyst, (B) a first distillation step wherein the reaction mixture formed by the above reaction step is cooled and introduced into a pressurized distillation column under pressure of at least 5 kg/cm$^2$G; refined dimethyl ether is obtained as a side stream; substance having a boiling point lower than that of dimethyl ether is distilled from the top; and the bottom is withdrawn, and (C) a second distillation step wherein said bottom is introduced into a second distillation column under pressure lower than the pressure of the pressurized distillation column; unreacted methanol is recovered as a side stream from the second distillation column; substance having a boiling point lower than that of methanol is distilled from the top; and the bottom is withdrawn, whereby (D) the unreacted methanol recovered from the second distillation step is recycled to the reaction step.

Now, the present invention will be described in detail with reference to a preferred embodiment as illustrated, in the accompanying drawing.

FIG. 1 is a flow sheet illustrating a preferred embodiment for the production of dimethyl ether from methanol according to the present invention.

In FIG. 1, reference numeral 1 designates a methanol tank, numeral 4 designates a reactor, numeral 7 designates a pressurized distillation column and numeral 14 designates a second distillation column.

Methanol starting material from the methanol tank 1 is evaporated and heated by an evaporator 3 and then supplied to the reaction step. The reaction is conducted under elevated pressure. In order that the reaction is conducted under elevated pressure, it is possible to pressurize methanol by a compressor after the evaporation of methanol. However, it is preferred to pressurize methanol in a liquid state by a pump 2, as shown in FIG. 1.

The reaction step comprises a reactor 4 packed with a solid acid catalyst. In this reaction step, dimethyl ether is produced from the methanol starting material by a vapour phase dehydration reaction.

From the viewpoint of introducing the reaction product into a distillation step under a pressurized condition, the reaction is conducted under pressure of at least 2 $kg/cm^2G$, and in order to avoid the necessity of providing heavy installations including the reactor, the reaction is conducted under pressure of not higher than 50 $kg/cm^2G$. More preferably, the reaction is conducted under pressure of from 3 to 30 $kg/cm^2G$, especially from 5 to 25 $kg/cm^2G$. In order to conduct the reaction under pressure, the reaction pressure may be maintained by introducing an inert gas. However, it is more advantageous to maintain the pressure by utilizing the vapour pressure of the reaction product under cooling by controlling the cooling temperature of the reaction gas.

The solid acid catalyst to be used in the reaction, may be any catalyst which is capable of forming dimethyl ether from methanol. However, from the viewpoints of the selectivity of the reaction and the catalytic activity, it is preferred to employ a crystalline or amorphous compound of alumina-type or silica-type other than zeolite, more preferably an alumina catalyst and a silica alumina catalyst. Particularly preferred is a γ-alumina catalyst.

The reaction temperature is selected within a range where the methanol starting material and the reaction products are in gaseous states. The reaction temperature is usually from 120° to 450° C. However, the reaction temperature should preferably be as low as possible, since thermodynamically the equillibrium conversion is higher and the selectivity tends to be improved at a lower temperature.

As the reaction method, a vapour phase flow system is most suitable wherein methanol vapour is directly, or after being diluted with an inert gas, introduced into the reactor 4 of e.g. heat-insulating type, multi-stage center cooling type or multi-tubular type, packed with the above-mentioned catalyst, and after the reaction, the reaction mixture is then introduced into the first distillation step.

In the first distillation step, the reaction mixture is cooled by a cooler 5 to a gas state, a gas-liquid mixed state or a liquid state, and after adjusting the pressure by e.g. a pressure control valve 6, the reaction product is fractionated in the pressurized distillation column 7 under pressure of at least 5 $kg/cm^2G$.

Further, in order to efficiently recover the heat of the reaction, it is preferred to conduct the cooling of the reaction mixture in a heat exchanging manner to preheat the methanol starting material, before cooling the reaction mixture by the cooler 5. Moreover, from the viewpoints of the separation efficiency of the reaction mixture and the thermal efficiency in the process, it is preferred to introduce the reaction mixture into the pressurized distillation column 7 in such a state that the reaction mixture is condensed in an amount of from 10 to 90% by weight, more preferably from 20 to 80% by weight, based on the total amount of methanol, water and dimethyl ether in the mixture.

In connection with the pressure control at the time of introducing the reaction mixture to the pressurized distillation column 7, the major proportion of the reaction product is liquefied by a usual cooling operation, and accordingly the reaction product may simply be pressurized by a pump. Further, in a case where the reaction pressure is higher than the pressure in the pressurized distillation column 7, it is unnecessary to pressurize the reaction product, and it is advantageous to pressurize the pressurized distillation column by utilizing the pressurized condition in the reaction zone to the maximum extent. This means that the pressure of the reaction zone should be maintained as far as possible except for the natural pressure drop resulting from the transfer of the substance or unavoidable pressure loss under the given conditions such as the pressure loss at the time of withdrawing a part of the non-condensed gas during the cooling operation. Accordingly, when the reaction pressure is set to be higher than the pressure of the pressurized distillation column 7, the pressure control of the reaction product can be made simply by means of a pressure control valve 6 as shown in FIG. 1, and no special equipment is required.

The pressurized distillation column to which the cooled reaction product is introduced, may be a packed column or a multi-stage column, and the pressure is maintained at a level of at least 5 $kg/cm^2G$ by the pressure control valve 9 or by introducing an inert gas to the top of the column. If the pressure is less than 5 $kg/cm^2G$, the cost for the cooling by the cooler 5 will be enormous and impractical since the boiling point of the dimethyl ether is $-23.6°$ C. Refined dimethyl ether is obtained as a side stream in the pressurized distillation column 7, condensed by a dimethyl ether condenser 10 and collected in a dimethyl ether tank 11. At the same time, from the top of the column, substance having a boiling point lower than that of dimethyl ether is distilled together with a part of dimethyl ether and purged through a reflux condenser 8 and the pressure control valve 9. Further, the bottom composed of unreacted methanol, formed water and by-products having a boiling point higher than dimethyl ether, is withdrawn and introduced into the second distillation step via a reboiler 12 and a liquid level control valve 13.

The second distillation step comprises a second distillation column 14 under pressure lower than the pressure of the pressurized distillation column 7 and at least atmospheric pressure. In this second distillation column, the bottom discharged from the first distillation step is subjected to separation, whereby almost pure unreacted methanol is distilled as a side stream and recovered via a methanol condenser 16 into a recovery methanol tank 17. At the time of this separation, from the top of the column, by-products having boiling points lower than the boiling point of methanol and higher than the boiling point of dimethyl ether are purged through a reflux condenser 15, and from the bottom of the column, formed water and by-products having boiling points higher than the boiling point of methanol, are discharged via a reboiler 19 and a discharge pump 20. The methanol recovered by this step will be recycled by a methanol recycling pump 18 to the reaction system, whereby the methanol starting material can be converted to dimethyl ether in good yield.

As mentioned above, the second distillation column 14 is maintained at pressure lower than the pressure of the pressurized distillation column 7, whereby no pressure controlling operation will be required when the distillation is conducted under atmospheric pressure, or even when the distillation is conducted under pressure, no such an apparatus as a pump or compressor is required and the pressure control may be conducted simply by the pressure control valve at the time of introducing the bottom.

According to the present invention, pure dimethyl ether suitable for use as a propellant can be obtained simply by the combination of two purification steps, and the recovered methanol can be reused as the starting material for the reaction, whereby dimethyl ether can be produced in extremely high overall yield relative to the consumption of the methanol starting material. Further, as the starting material, not only synthetic methanol but also by-product methanol containing substantial amount of impurities, generated e.g. at the time of the production of a polyester, may be employed, since by-products attributable to such impurities can be readily separated from dimethyl ether and the recovered methanol. Thus, the process of the present invention is practically superior as a process whereby dimethyl ether can be produced always in high purity irrespective of the degree of the purity of the starting material.

Further, since the dehydration reaction and the first distillation step is conducted in a pressurized system, the pressure control can simply be made by a pump or a pressure control valve without necessity of providing a step of liquefying the reaction mixture by low temperature cooling or liquefying the reaction mixture by the compression by means of a compressor which is required at the time of introducing the reaction mixture to the distillation step when the dehydration reaction is conducted under atmospheric pressure. Accordingly, a number of movable parts will be less as compared with the conventional process, and labor required for maintaining the apparatus can be minimized.

Now, the present invention will be described in further detail with reference to an Example.

EXAMPLE

Into a reactor packed with 0.1 m$^3$ of γ-alumina catalyst containing 0.08% by weight of Na$_2$O and heated to a temperature of from 250° to 350° C. by a heating medium, methanol pressurized in a liquid state and subsequently evaporated and heated, is supplied at a rate of 63 kg/hr, and the dehydration reaction was conducted under pressure of 11 kg/cm$^2$G.

The reaction product thereby obtained, was cooled, whereby a reaction mixture comprising 56.7% by weight of dimethyl ether, 22.5% by weight of water, 16% by weight of methanol and 4.8% by weight of other substances, was obtained. By this cooling, 40% by weight of the total amount of dimethyl ether, water and methanol was condensed and liquefied. This reaction mixture of gasliquid mixed phases, was introduced into a pressurized distillation column (inner diameter: 100 mm, 6 mmo Raschig rings, height of the packed layer: 3 m) which was maintained under pressure of 10 kg/cm$^2$G.

In the pressurized distillation column, the distillation was conducted at a reflux ratio of 2.0, whereby dimethyl ether having a purity of at least 99.9% was obtained at a rate of 35 kg/hr as a side stream, and at the same time, from the top of the column, dimethyl ether containing certain amounts of methane and ethane was distilled at a rate of 1 kg/hr. Further, the bottom comprising unreacted methanol, water and high boiling by-products was discharged and introduced at a flow rate of 27 kg/hr into a second distillation column under atmospheric pressure (inner diameter: 100 mm, 6 mmo Raschig rings, height of the packed layer: 5 m).

The second distillation column was operated at a reflux ratio of 2.0, whereby methanol containing no substantial impurities was recovered at a rate of 9 kg/hr as a side stream, and the recovered methanol was recycled to the reactor. Further, in the second distillation column, methanol containing a certain amount of methylformate is distilled at a rate of 1 kg/hr from the top, and waste water containing high boiling by-products was discharged at a rate of 17 kg/hr from the bottom of the column.

We claim:

1. A process for producing dimethyl ether, which is useful as a propellant, by dehydrating methanol and recovering dimethyl ether from the dehydrated product by distillation, which comprises:
   (a) dehydrating methanol in the vapor phase under a pressure of from 2 to 50 kg/cm$^2$ G over a solid acid catalyst;
   (b) cooling the obtained reaction mixture;
   (c) distilling said cooled reaction mixture in a first pressurized distillation column under a pressure of at least 5 kg/cm$^2$ G, whereby substances having a boiling point less than dimethyl ether are removed from the top of said column, refined dimethyl ether is removed as a side stream from said column and the bottoms of said column are withdrawn;
   (d) introducing said bottoms into a second distillation column;
   (e) distilling said bottoms in a second distillation column under a pressure lower than the pressure in the first distillation column, whereby substances having a boiling point lower than that of methanol are removed from the top of said second distillation column, unreacted methanol is recovered as a side stream from said second distillation column and the bottoms of said second distillation column are withdrawn; and
   (f) recycling said unreacted methanol to said dehydration reaction step.

2. The process according to claim 1, wherein the solid acid catalyst is an alumina catalyst and/or a silica catalyst other than zeolite.

3. The process according to claim 1, wherein the dehydration reaction is conducted at a temperature of from 120° to 450° C.

4. The process according to claim 1, wherein the dehydration reaction is conducted under pressure of from 3 to 30 kg/cm$^2$G.

5. The process according to claim 1, wherein the methanol reactant for step (a) is pressurized in the liquid state, then evaporated and supplied to the reaction step.

6. The process according to claim 1, wherein in step (b), the reaction mixture is cooled such that from 10 to 90% by weight of the reaction mixture is condensed, and then the reaction mixture is introduced into the first pressurized distillation column.

7. The process according to claim 1, wherein in step (c), the reaction mixture is introduced into said first pressurized distillation column without pressurizing the reaction mixture.

8. The process according to claim 9, wherein the methanol is a by-product methanol.

9. The process according to claim 6, wherein from 20–80% by weight of the reaction mixture is condensed.

* * * * *